US009600995B2

(12) United States Patent
Gaidar et al.

(10) Patent No.: US 9,600,995 B2
(45) Date of Patent: Mar. 21, 2017

(54) WEARABLE ELECTRONIC DEVICE TO PROVIDE INJURY RESPONSE

(71) Applicant: Intel Corporation, Santa Clara, CA (US)

(72) Inventors: Tamara Gaidar, Haifa (IL); Glen J. Anderson, Beaverton, OR (US); Yoav Talgam, Haifa (IL); Stephen Brown, Hillsboro, OR (US); Ido Lapidot, Haifa (IL); Oded Agam, Herzliya (IL)

(73) Assignee: Intel Corporation, Santa Clara, CA (US)

( * ) Notice: Subject to any disclaimer, the term of this patent is extended or adjusted under 35 U.S.C. 154(b) by 0 days.

(21) Appl. No.: 14/752,764

(22) Filed: Jun. 26, 2015

(65) Prior Publication Data

US 2016/0379461 A1 Dec. 29, 2016

(51) Int. Cl.

| | |
|---|---|
| ***A61B 5/00*** | (2006.01) |
| ***G08B 21/04*** | (2006.01) |
| ***A41D 1/00*** | (2006.01) |
| ***A43B 3/00*** | (2006.01) |

(52) U.S. Cl.

CPC ......... *G08B 21/0453* (2013.01); *A41D 1/002* (2013.01); *A43B 3/0005* (2013.01)

(58) Field of Classification Search

CPC .... A61B 5/6804; A61B 5/6802; A61B 5/6803

USPC .......................................................... 340/665

See application file for complete search history.

(56) References Cited

U.S. PATENT DOCUMENTS

| | | | | |
|---|---|---|---|---|
| 2004/0209233 | A1* | 10/2004 | Ray | G09B 23/28 434/238 |
| 2014/0266752 | A1* | 9/2014 | John | A61B 5/1117 340/665 |
| 2015/0177939 | A1 | 6/2015 | Anderson et al. | |

OTHER PUBLICATIONS

Anthony, Sabastian, "CES 2014: Intel Abandons Smartphones, Focuses on Wearable Computing and Tablets," http://www.extremetech.com/extreme/174168-ces-2014-intel-abandons-the-smartphone-ship-focuses-on-wearable-computing-and-tablets, Jan. 7, 2014.

* cited by examiner

*Primary Examiner* — Kevin Kim

(74) *Attorney, Agent, or Firm* — Blakely, Sokoloff, Taylor & Zafman LLP

(57) ABSTRACT

Embodiments are generally directed to a wearable electronic device providing injury response. A wearable electronic device may include an injury detection unit that includes one or more sensors, and a central computing unit to receive sensor data from the one or more sensors to detect one or more injuries or potential injuries based at least in part on the received sensor data. The wearable electronic device further includes an injury response unit to provide a response to the one or more injuries or potential injuries.

20 Claims, 6 Drawing Sheets

WEARABLE ELECTRONIC DEVICE TO PROVIDE INJURY RESPONSE

TECHNICAL FIELD

Embodiments described herein generally relate to the field of electronic devices and, more particularly, to a wearable electronic device to provide injury response.

BACKGROUND

In addition to usages in many other types of clothing items, wearable electronic devices have been implemented for certain athletic and health functions. For example, tracking devices can assist in determining the extent of athletic activity, such as the number of steps a person has taken, the heart rate of the person during activity, and related health or athletic information.

With the miniaturization and reduction in cost of technology, the wearable devices may be incorporated into certain wearable garments, rather than being in separate electronic devices that are clipped on to clothing or otherwise carried.

Athletic activities carry with them the risk of injury and accident. In emergency circumstances, the needs of individuals shift from issues such as athletic tracking provided by conventional devices to immediate issues of addressing medical care, such as in the needs of emergency medical provides to address trauma and other medical issues.

BRIEF DESCRIPTION OF THE DRAWINGS

Embodiments described here are illustrated by way of example, and not by way of limitation, in the figures of the accompanying drawings in which like reference numerals refer to similar elements.

DETAILED DESCRIPTION

Embodiments described herein are generally directed to a wearable electronic device providing injury response.

For the purposes of this description:

"Wearable electronic device", also referred to as a "wearable device" or "wearable", means an electronic device being configured to be worn by a user. As used herein, wearable electronic device includes a "wearable garment", meaning an item of clothing or other garment that includes an integrated or embedded electronics.

"Garment" means any item that is worn by a human user, including, but not limited to, clothing of any kind, hats or other headwear, gloves or mittens, shoes or boots, scarves, belts, or decorative wearable items.

In some embodiments, a wearable electronic device, including a wearable garment, provides for injury response. In some embodiments, a wearable electronic device is operable to provide a response based on injuries to the body, wherein the response may include adjustments to identify and report injury and adjustments to protect the body of the user, which may include protection of the location of an injury or engaging protection to prevent injury from occurring.

In some embodiments, a wearable electronic device includes embedded sensors and active elements that operable to respond with various actions to physically protect users, where the actions may include:

(1) A blow to the body may be recorded and displayed by changing the color of a wearable garment at the site of the blow;

(2) Sensors in the garment could detect bruises or bleeding and represent the wound to the skin on the outside of the garment;

(3) A specific medical or health issue could be identified, such as diaper rash being displayed on the outside of a diaper (where (1) to (3) may be referred to generally as place of injury indicators);

(4) If a user is falling or otherwise may suffer an impact, inflatable sections, or air bags, in the garment could activate to protect the body of the user;

(5) A wearable garment may automatically provide adjustment to prevent movements that could be dangerous (such as reducing movement in an arm healing from a break);

(6) The wearable electronic device may provide for adjustments in response to user settings. In an example, wearable settings that are accessible by parents may provide for control of aspects of a young child's clothing to allow the parent to control safety factors.

Figure 1:
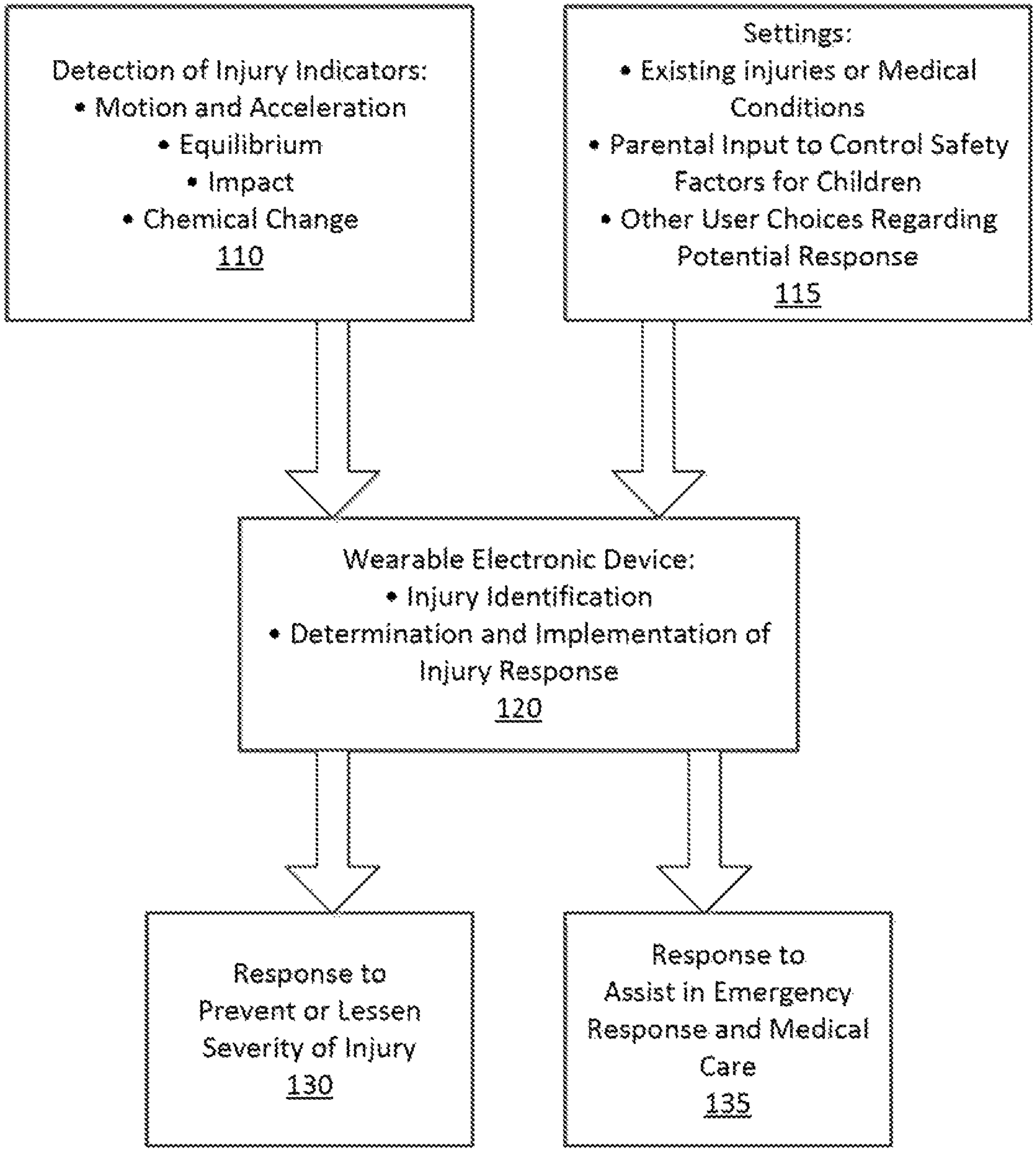
FIG. 1 is an illustration of operation of a wearable electronic device to provide injury response according to an embodiment.

FIG. 1 is an illustration of operation of a wearable electronic device to provide injury response according to an embodiment. In some embodiments, a wearable electronic device provides for detection of injury indications 110, where the injury indications may include one or more of motion and acceleration levels and changes, equilibrium change, impact levels, and chemical changes, such as the evidence of blood.

In some embodiments, the wearable electronic device further accesses one or more settings that are related to injury response 115, wherein the settings may include data regarding existing injuries or medical conditions, parental input to control safety factors children and other user choices regarding potential injury response.

In some embodiments, based on the injury indicators and settings, the wearable electronic device provides identification of a type and location of an injury, and determination and implementation of an injury response 120.

In some embodiments, the injury response includes one or both or a response to prevent or lessen severity of injury 130, and a response to assist in emergency response and medical care 135.

Figure 2:
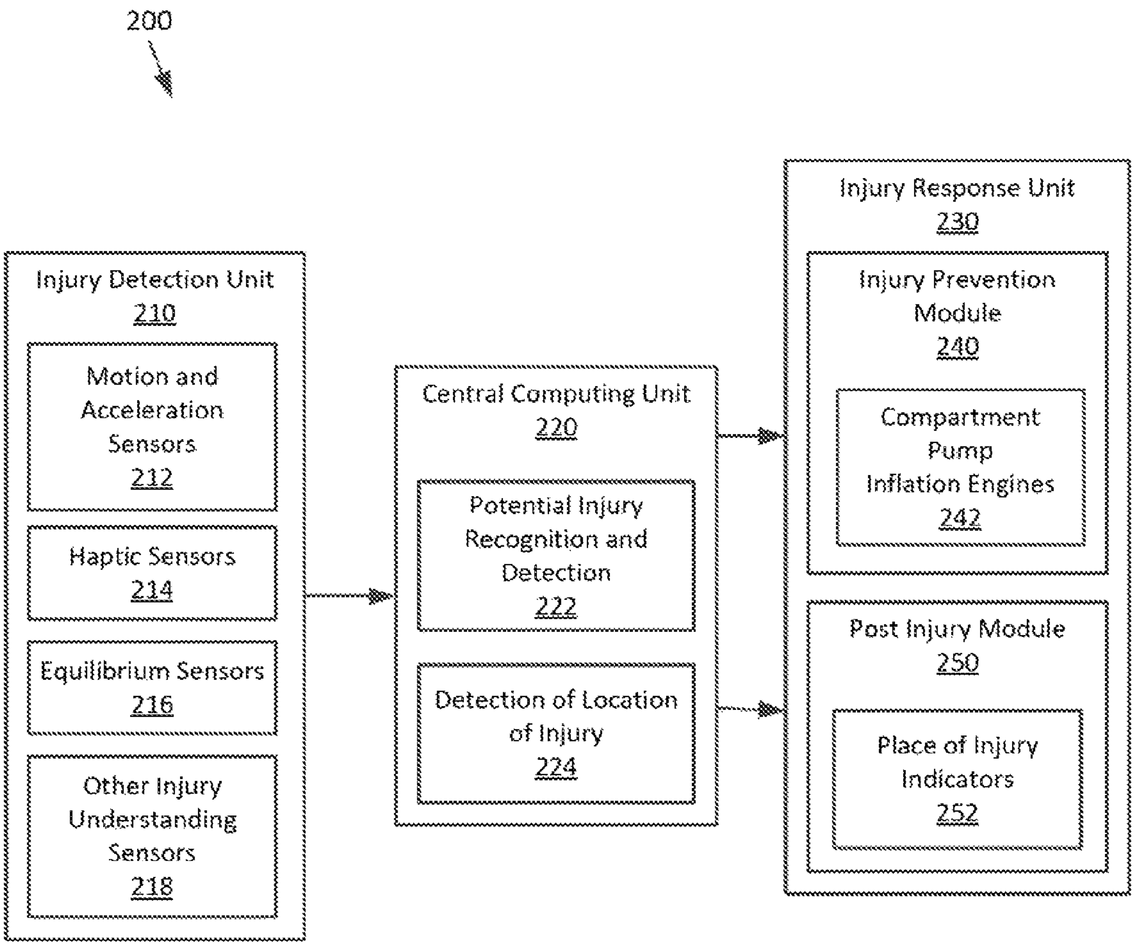
FIG. 2 is an illustration of operation of components of a wearable electronic device to provide injury response according to an embodiment.

FIG. 2 is an illustration of operation of components of a wearable electronic device to provide injury response according to an embodiment. In some embodiments, a wearable electronic device includes an injury detection unit 210 to detect injuries, which may include detection of injuries that have occurred or that may occur; a central computing unit 220 to process data from the injury detection unit 210; and an injury response unit 230 including one or more of an injury prevention module 240; and a post injury module 250.

In some embodiments, the injury detection unit 210 includes motion and acceleration sensors 212 to detect levels and changes in motion and acceleration (where large changes in motion or rapid changes in acceleration may indicate conditions that may generate an injury); haptic sensor 214 to sense forces on the sensor; equilibrium sensors 216 to detect apparent changes in equilibrium of a user; and other injury understanding sensors 218.

In some embodiments, the central computing unit 220 receives the sensor data from the sensors of the injury detection unit 210, provides for potential injury recognition and detection 222 and detection of location of injury 224.

In some embodiments, the injury prevention module 240 provides for one or more actions to prevent or lessen injury, where the elements of the module may include, but are not limited to, compartment pump inflation engines 242 to inflate one or more portions of the wearable electronic device to protect the user from injury.

In some embodiments, the post injury module 250 provides for place of injury indicators 252, such as changing the appearance of the wearable garment to indicate an injury. In some embodiments, the change in appearance may vary depending on the type of injury detected.

In some embodiments, injury response may include recordation of data from the injury to assist medical personnel. In an embodiment, the injury data may be accessed wirelessly by medical personnel.

In some embodiments, the response may include the generation of a signal, including a radio signal, regarding the injury. In some embodiments, the response may include sending the signal via a wired or wireless interface to a linked smart phone (or other mobile computing device), wherein the smart phone may then make an automatic phone call to request emergency response.

Figures 3A, 3B:
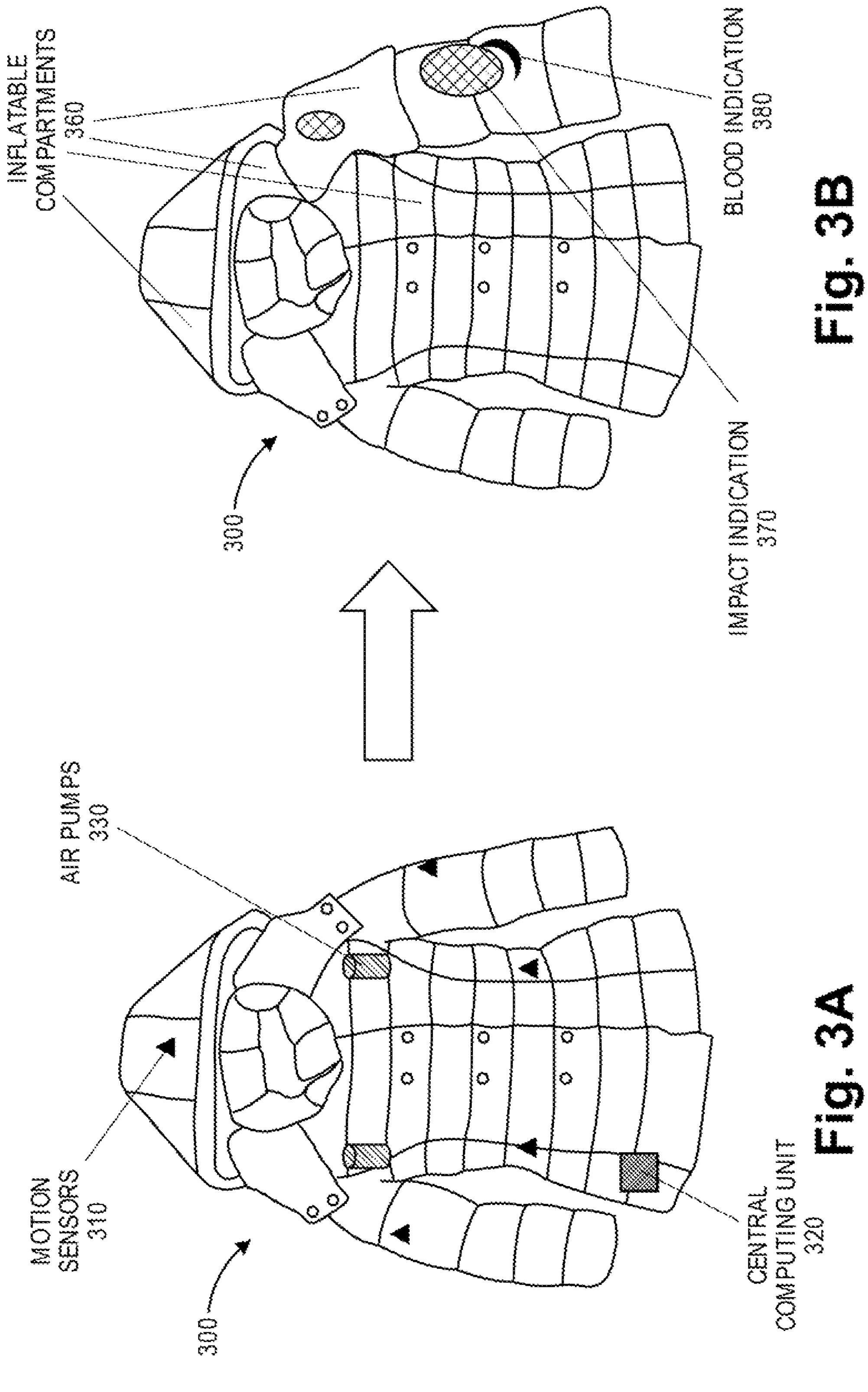
FIGS. 3A and 3B provide illustrations of a wearable garment in the form of a parka to provide injury response according to an embodiment.

FIGS. 3A and 3B provide illustrations of a wearable garment in the form of a parka to provide injury response according to an embodiment. FIG. 3A illustrates the wearable garment in a pre-injury condition, and FIG. 3B illustrates the wearable garment in a post-injury condition. In some embodiments, a wearable garment 300 is a coat such as a ski parka that is used in downhill skiing. In some embodiments, as illustrated in FIG. 3A, the wearable garment 300 includes one or more sensors, including, but not limited to, motion sensors 310 to detect motion that may be indicative of an injury; a central computing unit 320, and air pumps 330 to inflate one or more sections of the wearable garment 300 to protect a user from injury. It is noted that, while the inflation elements are generally referred to as air pumps, the inflation elements may include any element that causes the inflation of a compartment, as further described below.

In some embodiments, as illustrated in FIG. 3B, the wearable garment 300 includes inflatable compartments 360, one or more of which are inflated when an injury condition is detected. In some embodiments, the wearable garment includes one or more injury indications, where the injury indications may include an impact indication 370 to indicate an area in which an impact has occurred, and a blood indication 380 to indicate where bleeding has occurred. In some embodiments, the injury indications are changes in the outward appearance of the wearable garment produced by electronic signal or other action directed by the central computing unit 320. In some embodiments, the sensors of the wearable garment may further include one or more outward facing visual sensors (such as cameras) to detect impending impacts with other objects, thus allowing the central computing unit to inflate the inflatable compartments 360 prior to impact to prevent or lessen injury.

In some embodiments, the components of a wearable garment such as parka 300 illustrated in FIGS. 3A and 3B enable the system to operate as follows:

(1) A motion sensor array provides for detection of falling.

(2) A computing unit to receive data from the sensors and determine whether a fall, collision, or other injury-causing event is occurring.

(3) Inflatable compartments in the jacket inflate to provide protection. Such elements may be implemented with a chemical process that rapidly generates nitrogen gas to fill the airbag, using compressed nitrogen or argon gas with a valve that is activated before impact, or other similar inflation operation. The amount of gas needed would be small to fill such small compartments. In some embodiments, the wearable garment may include tubes to connect pumps to the inflatable compartments. In some embodiments, compartments may alternatively be self-contained with their own compressed gas in cushioned containers. The computing unit is connected with the pumps to control the pump operation.

(4) Chemical and pressure sensors embedded in the garment allow for detection of forces and blood. MEMS (microelectromechanical systems) pressure sensors or piezoelectric sensors (which can also be implemented with MEMS) may enable measurement of external pressures that meet the garment. In some embodiments, the system determines whether pressures were severe enough to warrant display.

(5) Inflation of compartments utilizing self-inflating elements. The compartments may be capable of self-inflation due to the open-cell foam that fills the internal cavity.

Figure 4A:
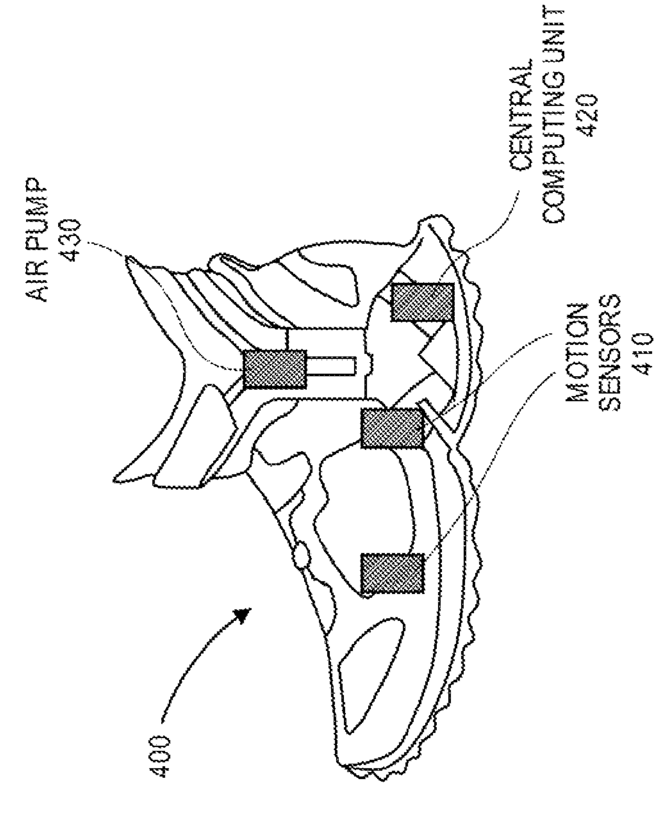
FIGS. 4A and 4B provide illustrations of a wearable garment in the form of an athletic shoe to provide injury response according to an embodiment.
Figure 4B:
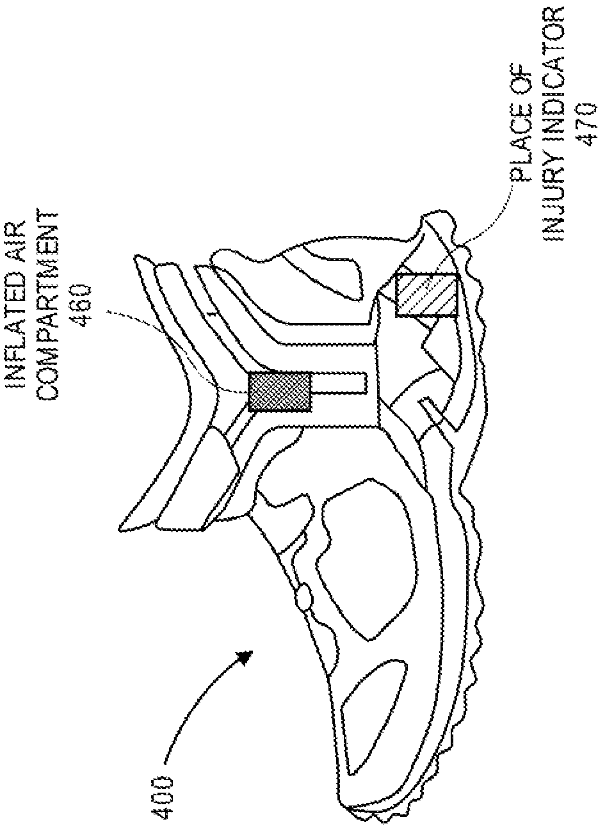

FIGS. 4A and 4B provide illustrations of a wearable garment in the form of an athletic shoe to provide injury response according to an embodiment. FIG. 4A illustrates the athletic shoe in a pre-injury condition, and FIG. 4B illustrates the athletic shoe in a post-injury condition. In some embodiments, a wearable garment 400 is an athletic shoe. In some embodiments, as illustrated in FIG. 4A, the athletic shoe 400 includes motion sensors 410, such as embedded in the sole of the shoe 400, to detect motion that may be indicative of an injury; a central computing unit 420, and an air pump 430 to inflate one or more sections of the athletic shoe to protect a user from injury.

In some embodiments, as illustrated in FIG. 4B, the athletic shoe 400 includes an inflated air compartment 460. In some embodiments, the athletic shoe 400 includes a place of injury indicator 470 to indicate the location of an injury.

Figure 5:
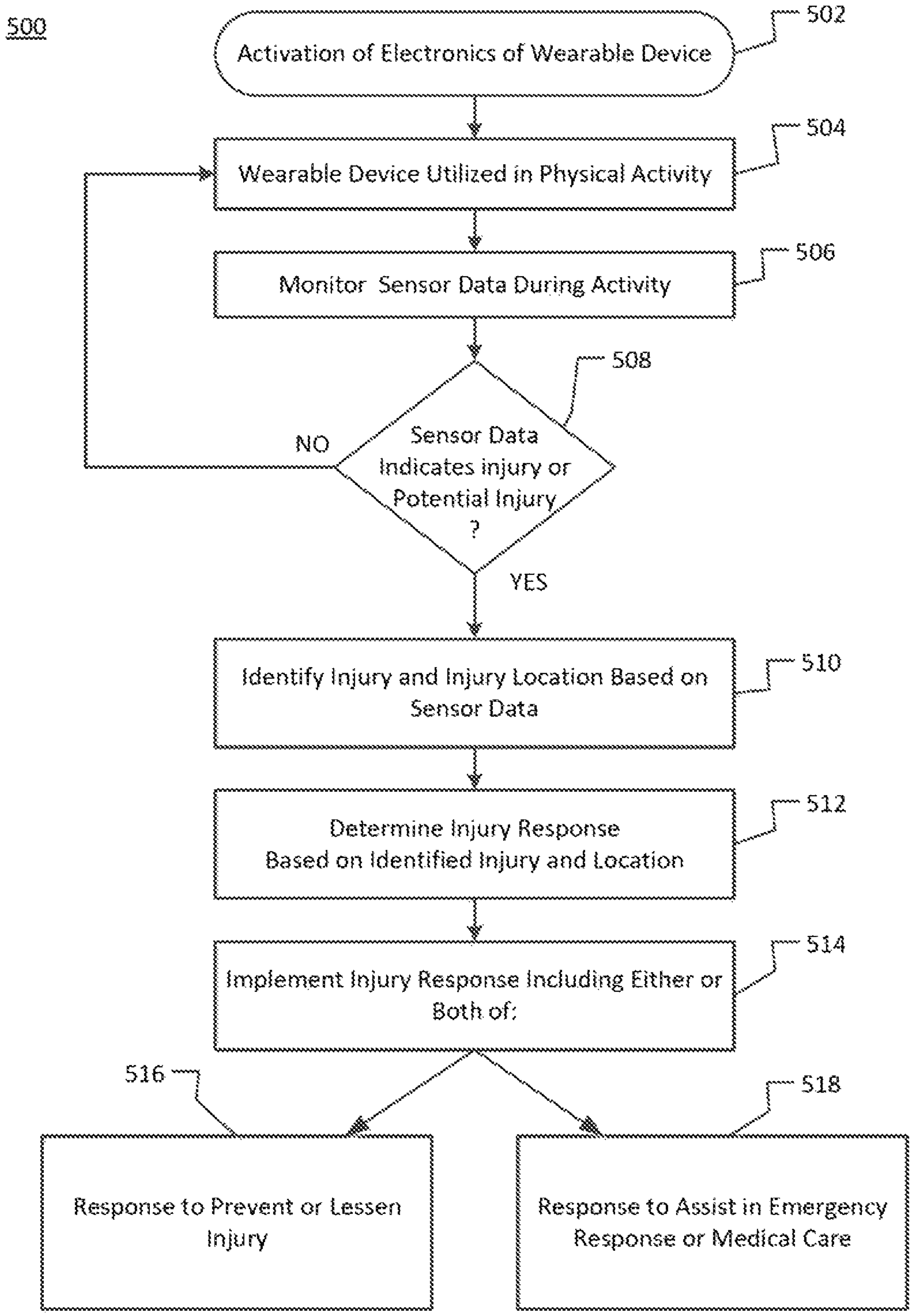
FIG. 5 is a flowchart to illustrate a process for a wearable electronic device to provide injury response according to an embodiment.

FIG. 5 is a flowchart to illustrate a process for a wearable electronic device to provide injury response according to an embodiment. In some embodiments, a process 500 includes, upon activation of the electronics of a wearable device 502 (such as illustrated in FIGS. 1-4), which may occur automatically with the start of an activity or may require some action to turn the electronics on (and in some embodiments to link the wearable device with a smart phone or other mobile computing device), a user may utilize the wearable device in a physical activity 504. For example, the parka wearable device 300 illustrated in FIGS. 3A and 3B may be utilized in skiing or the shoe wearable device 400 illustrated in FIGS. 4A and 4B may be utilized in running.

In some embodiments, the wearable device is to monitor sensor data during the physical activity 506, such as the monitoring of data from motion sensors 310 illustrated in FIG. 3A or motion sensors 410 illustrated in FIG. 4A. In some embodiments, if the sensor data indicates an injury or a potential injury 508, the wearable device is to identify the injury and injury location based on the sensor data 510 and is to determine injury response based on the identified injury and injury location 512. In some embodiments, the sensor data may include visual data from one or more outward facing cameras or other visual sensors, wherein the visual data may be utilized to detect an impending impact.

In some embodiments, the wearable device is to implement the determined injury response 514, including either or both of a response to prevent or lessen injury 516, such as engaging inflatable portions of the wearable device, or a response to assist in emergency response or medical care 518, such as providing injury indicators on the surface of the wearable device. In some embodiments, the implementation of the injury response may include determining to inflate the inflatable portions of the wearable device prior to an impending impact to protect the user. In some embodiments, a response to an injury includes sending data to a linked mobile computing device, such as a smart phone, wherein the smart phone may record injury information or provide an automatic call for emergency care.

Figure 6:
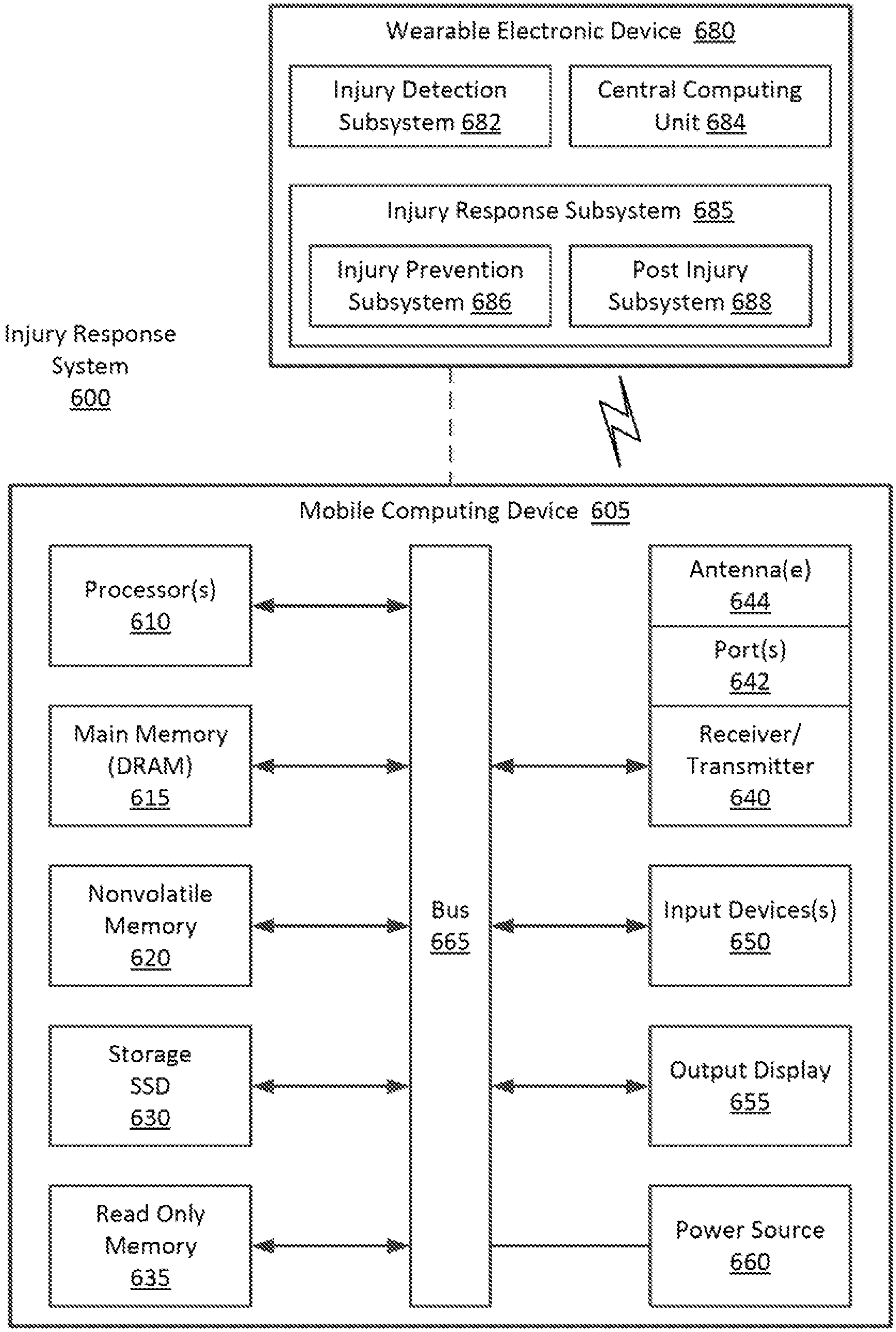
FIG. 6 is an illustration of an embodiment of an injury response system including a wearable electronic device according to an embodiment.

FIG. 6 is an illustration of an embodiment of an injury response system including a wearable electronic device according to an embodiment. In this illustration, certain standard and well-known components that are not germane to the present description are not shown. Elements shown as separate elements may be combined, including, for example, an SoC (System on Chip) combining multiple elements on a single chip.

In some embodiments, an injury response system 600 includes a wearable electronic device 680 that is linked via an interface with a mobile computing device 605, where the mobile computing may be, but is not limited to, a smart phone. In some embodiments, the wearable electronic device 680 may be as illustrated in FIGS. 1 through 4B. In some embodiments, the wearable electronic device 680 includes an injury detection subsystem 682, a central computing unit 684, and an injury response subsystem 685 including one or more of an injury prevention subsystem 686 and a post injury subsystem 688.

In some embodiments, the wearable electronic device 680 may be linked by a wireless or wired interface connection with a mobile computing device 605 that provides for processing, data, or communication support for the wearable electronic device 680.

In some embodiments, the mobile computing device 605 may include a processing means such as one or more processors 610 coupled to one or more buses or interconnects, shown in general as bus 665. The processors 610 may comprise one or more physical processors and one or more logical processors. In some embodiments, the processors may include one or more general-purpose processors or special-processor processors.

The bus 665 is a communication means for transmission of data. The bus 665 is illustrated as a single bus for simplicity, but may represent multiple different interconnects or buses and the component connections to such interconnects or buses may vary. The bus 665 shown in FIG. 6 is an abstraction that represents any one or more separate physical buses, point-to-point connections, or both connected by appropriate bridges, adapters, or controllers.

In some embodiments, the mobile computing device 605 further comprises a random access memory (RAM) or other dynamic storage device or element as a main memory 615 for storing information and instructions to be executed by the processors 610. Main memory 615 may include, but is not limited to, dynamic random access memory (DRAM).

The mobile computing device 605 also may comprise a non-volatile memory 620; a storage device such as a solid state drive (SSD) 630; and a read only memory (ROM) 635 or other static storage device for storing static information and instructions for the processors 610.

In some embodiments, the mobile computing device 605 includes one or more transmitters or receivers 640 coupled to the bus 665. In some embodiments, the mobile computing device 605 may include one or more antennae 644, such as dipole or monopole antennae, for the transmission and reception of data via wireless communication using a wireless transmitter, receiver, or both, and one or more ports 642 for the transmission and reception of data via wired communications. Wireless communication includes, but is not limited to, Wi-Fi, Bluetooth™, near field communication, and other wireless communication standards. Wired or wireless communications may include communications with the wearable electronic device 680.

In some embodiments, the mobile computing device 605 includes one or more input devices 650 for the input of data, including hard and soft buttons, a joy stick, a mouse or other pointing device, a keyboard, voice command system, or gesture recognition system.

In some embodiments, the mobile computing device 605 includes an output display 655, where the display 655 may include a liquid crystal display (LCD) or any other display technology, for displaying information or content to a user. In some environments, the display 655 may include a touch-screen that is also utilized as at least a part of an input device 650. Output display 655 may further include audio output, including one or more speakers, audio output jacks, or other audio, and other output to the user.

The mobile computing device 605 may also comprise a battery or other power source 660, which may include a solar cell, a fuel cell, a charged capacitor, near field inductive coupling, or other system or device for providing or generating power in the mobile computing device 605. The power provided by the power source 660 may be distributed as required to elements of the mobile computing device 605.

In the description above, for the purposes of explanation, numerous specific details are set forth in order to provide a thorough understanding of the described embodiments. It will be apparent, however, to one skilled in the art that embodiments may be practiced without some of these specific details. In other instances, well-known structures and devices are shown in block diagram form. There may be intermediate structure between illustrated components. The components described or illustrated herein may have additional inputs or outputs that are not illustrated or described.

Various embodiments may include various processes. These processes may be performed by hardware components or may be embodied in computer program or machine-executable instructions, which may be used to cause a general-purpose or special-purpose processor or logic circuits programmed with the instructions to perform the processes. Alternatively, the processes may be performed by a combination of hardware and software.

Portions of various embodiments may be provided as a computer program product, which may include a computer-readable medium having stored thereon computer program instructions, which may be used to program a computer (or other electronic devices) for execution by one or more processors to perform a process according to certain embodiments. The computer-readable medium may include, but is not limited to, magnetic disks, optical disks, compact disk read-only memory (CD-ROM), and magneto-optical disks, read-only memory (ROM), random access memory (RAM), erasable programmable read-only memory (EPROM), electrically-erasable programmable read-only memory (EEPROM), magnet or optical cards, flash memory, or other type of computer-readable medium suitable for storing electronic instructions. Moreover, embodiments may also be downloaded as a computer program product, wherein the program may be transferred from a remote computer to a requesting computer.

Many of the methods are described in their most basic form, but processes can be added to or deleted from any of the methods and information can be added or subtracted from any of the described messages without departing from the basic scope of the present embodiments. It will be apparent to those skilled in the art that many further modifications and adaptations can be made. The particular embodiments are not provided to limit the concept but to illustrate it. The scope of the embodiments is not to be determined by the specific examples provided above but only by the claims below.

If it is said that an element "A" is coupled to or with element "B," element A may be directly coupled to element B or be indirectly coupled through, for example, element C. When the specification or claims state that a component, feature, structure, process, or characteristic A "causes" a component, feature, structure, process, or characteristic B, it means that "A" is at least a partial cause of "B" but that there may also be at least one other component, feature, structure, process, or characteristic that assists in causing "B." If the specification indicates that a component, feature, structure, process, or characteristic "may", "might", or "could" be included, that particular component, feature, structure, process, or characteristic is not required to be included. If the specification or claim refers to "a" or "an" element, this does not mean there is only one of the described elements.

An embodiment is an implementation or example. Reference in the specification to "an embodiment," "one embodiment," "some embodiments," or "other embodiments" means that a particular feature, structure, or characteristic described in connection with the embodiments is included in at least some embodiments, but not necessarily all embodiments. The various appearances of "an embodiment," "one embodiment," or "some embodiments" are not necessarily all referring to the same embodiments. It should be appreciated that in the foregoing description of exemplary embodiments, various features are sometimes grouped together in a single embodiment, figure, or description thereof for the purpose of streamlining the disclosure and aiding in the understanding of one or more of the various novel aspects. This method of disclosure, however, is not to be interpreted as reflecting an intention that the claimed embodiments requires more features than are expressly recited in each claim. Rather, as the following claims reflect, novel aspects lie in less than all features of a single foregoing disclosed embodiment. Thus, the claims are hereby expressly incorporated into this description, with each claim standing on its own as a separate embodiment.

In some embodiments, a wearable electronic device includes an injury detection unit including one or more sensors; a computing unit to receive sensor data from the one or more sensors to detect one or more injuries or potential injuries based at least in part on the received sensor data; and an injury response unit to provide a response to the one or more injuries or potential injuries.

In some embodiments, the injury response unit includes one or more of an injury prevention module and a post injury module.

In some embodiments, the injury prevention module includes one or more units to prevent injury or further injury by a user. In some embodiments, the one or more units to prevent injury or further injury include one or more inflatable compartments and one or more inflation engines to provide for inflation of the inflatable compartments.

In some embodiments, the post injury module includes one or more place of injury indicators. In some embodiments, the one or more place of injury indicators include an impact indicator to indicate a location where an impact has been detected by the computing unit. In some embodiments, the one or more place of injury indicators include a blood indicator to indicate a location where bleeding has been detected by the computing unit.

In some embodiments, the one or more sensors include one or more of: a motion sensor; an acceleration sensor; a chemical sensor to detect the presence of blood; a pressure sensor to detect impact forces; or a visual sensor to detect an impending impact.

In some embodiments, a non-transitory computer-readable storage medium having stored thereon data representing sequences of instructions that, when executed by a processor, cause the processor to perform operations including monitoring data received from one or more sensors of a wearable electronic device during an activity; detecting by a computing unit one or more injuries or potential injuries for a user of the wearable electronic device based on the sensor data from the one or more sensors; and generating by the computing unit a response to the one or more injuries or potential injuries.

In some embodiments, the detection of one or more injuries or potential injuries includes identifying a type of injury and a location of injury.

In some embodiments, the response to the one or more injuries or potential injuries includes one or more of a response to prevent or lessen injury and a post injury response.

In some embodiments, providing a response to prevent or lessen injury includes inflating one or more inflatable compartments to provide injury protection.

In some embodiments, providing a post injury response includes enabling one or more place of injury indicators. In some embodiments, the one or more place of injury indicators includes an impact indicator to indicate a location where an impact has been detected by the computing unit. In some embodiments, the one or more place of injury indicators include a blood indicator to indicate a location where bleeding has been detected by the computing unit.

In some embodiments, a method includes monitoring data received from one or more sensors of a wearable electronic device during an activity; detecting by a computing unit one or more injuries or potential injuries for a user of the wearable electronic based on the sensor data from the one or more sensors; and generating by the computing unit a response to the one or more injuries or potential injuries.

In some embodiments, a wearable garment includes an injury detection subsystem including a plurality of sensors; a computing unit to receive sensor data from the plurality of sensors to detect one or more injuries or potential injuries based at least in part on the received sensor data; and an injury response subsystem to provide a response to the one or more injuries or potential injuries.

In some embodiments, the injury response subsystem includes one or more of an injury prevention subsystem to provide one or more actions to prevent or lessen injury; and a post injury subsystem to provide one or more actions to assist in emergency response and medical care.

In some embodiments, the injury prevention subsystem includes one or more inflatable compartments in the wearable garment.

In some embodiments, the post injury subsystem includes one or more place of injury indicators.

In some embodiments, the wearable garment further includes an interface for connection with a mobile computing device. In some embodiments, the wearable garment is to provide data to the mobile computing device upon detection of an injury.

In some embodiments, an apparatus includes means for monitoring data received from one or more sensors of a wearable electronic device during an activity; means for detecting by a computing unit one or more injuries or potential injuries for a user of the wearable electronic based on the sensor data from the one or more sensors; and means for responding to the one or more injuries or potential injuries.

In some embodiments, the means for detection of one or more injuries or potential injuries includes means for identifying a type of injury and a location of injury.

In some embodiments, the means for responding to the one or more injuries or potential injuries includes one or more of means for preventing or lessening injury and means for post injury response.

In some embodiments, the means for preventing or lessening injury includes means for inflating one or more inflatable compartments to provide injury protection.

In some embodiments, the means for post injury response includes means for providing place of injury indicators. In some embodiments, the means for providing place of injury indicators includes means for indicating a location where an impact has been detected by the computing unit. In some embodiments, the means for providing place of injury indicators includes means for indicating a location where bleeding has been detected.

What is claimed is:

1. A wearable electronic device comprising:

an injury detection unit including one or more sensors;

a computing unit to receive sensor data from the one or more sensors to detect one or more injuries or potential injuries to a user of the wearable electronic device based at least in part on the received sensor data, wherein the detection of one or more injuries or potential injuries includes identifying a type of injury and a location of injury; and an injury response unit to provide a response to the one or more injuries or potential injuries to the user of wearable electronic device that are detected by the computing unit, the injury response unit including a post injury module;

wherein the post injury module includes one or more place of injury indicators, each of the one or more place of injury indicators to change an appearance of the wearable electronic device to indicate a location of an injury to the user of the wearable electronic device.

2. The wearable electronic device of claim 1, wherein the injury response unit further includes an injury prevention module.

3. The wearable electronic device of claim 2, wherein the injury prevention module includes one or more units to prevent injury or further injury by the user.

4. The wearable electronic device of claim 3, wherein the one or more units to prevent injury or further injury to the user include one or more inflatable compartments and one or more inflation engines to provide for inflation of the inflatable compartments.

5. The wearable electronic device of claim 1, wherein the one or more place of injury indicators include an impact indicator to change the appearance of the wearable electronic device to indicate a location where an impact has been detected by the computing unit.

6. The wearable electronic device of claim 1, wherein the one or more place of injury indicators include a blood indicator to change the appearance of the wearable electronic device to indicate a location where bleeding has been detected by the computing unit.

7. The wearable electronic device of claim 1, wherein the one or more sensors include one or more of the following:

a motion sensor;

an acceleration sensor;

a chemical sensor to detect the presence of blood a pressure sensor to detect impact forces; or a visual sensor to detect an impending impact.

8. A non-transitory computer-readable storage medium having stored thereon data representing sequences of instructions that, when executed by a processor, cause the processor to perform operations comprising:

monitoring data received from one or more sensors of a wearable electronic device during an activity;

detecting by a computing unit one or more injuries or potential injuries to a user of the wearable electronic device based on the sensor data from the one or more sensors, wherein the detection of one or more injuries or potential injuries includes identifying a type of injury and a location of injury; and generating by the computing unit a response to the one or more injuries or potential injuries, the response to the one or more injuries or potential injuries including a post injury response;

wherein providing a post injury response includes enabling one or more place of injury indicators to change an appearance of the wearable electronic device to indicate a location of an injury.

9. The medium of claim 8, wherein the response to the one or more injuries or potential injuries to the user further includes a response to prevent or lessen injury.

10. The medium of claim 9, wherein providing a response to prevent or lessen injury to the user includes inflating one or more inflatable compartments to provide injury protection.

11. The medium of claim 8, wherein the one or more place of injury indicators include an impact indicator to indicate a location where an impact has been detected by the computing unit.

12. The medium of claim 8, wherein the one or more place of injury indicators include a blood indicator to indicate a location where bleeding has been detected by the computing unit.

13. A wearable garment comprising:

an injury detection subsystem including a plurality of sensors;

a computing unit to receive sensor data from the plurality of sensors to detect one or more injuries or potential injuries to a user of the wearable garment based at least in part on the received sensor data, wherein the detection of one or more injuries or potential injuries includes identifying a type of injury and a location of injury; and an injury response subsystem to provide a response to the one or more injuries or potential injuries that are detected by the computing unit, the injury response subsystem including a post injury subsystem to provide one or more actions to assist in emergency response and medical care;

wherein the post injury subsystem includes one or more place of injury indicators, each of the one or more place of injury indicators to change an appearance of the wearable garment to indicate a location of an injury to the user of the wearable garment.

14. The wearable garment of claim 13, wherein the injury response subsystem further includes the following:

an injury prevention subsystem to provide one or more actions to prevent or lessen injury to the user of the wearable garment.

15. The wearable garment of claim 14, wherein the injury prevention subsystem includes one or more inflatable compartments in the wearable garment.

16. The wearable garment of claim 13, further comprising an interface for connection with a mobile computing device.

17. The wearable garment of claim 16, wherein the wearable garment is to provide data to the mobile computing device upon detection of an injury to the user of the wearable garment.

18. The wearable garment of claim 13, wherein the one or more place of injury indicators include an impact indicator to change the appearance of the wearable garment to indicate a location where an impact has been detected by the computing unit.

19. The wearable garment of claim 13, wherein the one or more place of injury indicators include a blood indicator to change the appearance of the wearable garment to indicate a location where bleeding has been detected by the computing unit.

20. The wearable garment of claim 13, wherein the plurality of sensors includes one or more of the following:

a motion sensor;

an acceleration sensor;

a chemical sensor to detect the presence of blood a pressure sensor to detect impact forces; or a visual sensor to detect an impending impact.

* * * * *